United States Patent [19]

Baker

[11] Patent Number: 5,300,712

[45] Date of Patent: Apr. 5, 1994

[54] HOMOGENEOUS CATALYTIC HYDRODECHLORINATION OF CHLOROCARBONS

[75] Inventor: Ralph T. Baker, Wilmington, Del.

[73] Assignee: E. I. Du Pont de Nemours and Company, Wilmington, Del.

[21] Appl. No.: 68,499

[22] Filed: May 27, 1993

[51] Int. Cl.$^5$ ............................................. C07C 17/10
[52] U.S. Cl. ................................................. 570/176
[58] Field of Search ........................................ 570/176

[56] References Cited

U.S. PATENT DOCUMENTS

| | | | |
|---|---|---|---|
| 5,053,564 | 10/1991 | Cheminal et al. | 570/176 |
| 5,068,473 | 11/1991 | Kellner et al. | 570/176 |
| 5,136,113 | 8/1992 | Rao | 570/176 |

FOREIGN PATENT DOCUMENTS 0308923  3/1989  European Pat. Off. ............ 570/176

1578933  11/1980  United Kingdom .

OTHER PUBLICATIONS

Lokteva et al., *Izv. Akad. Nauk. SSSR, Ser. Khim*, 3:539–542 (1989).

Ferruhgelli and Horvath, *J. Chem. Soc., Chem. Commun.*, pp. 806–807 (1992).

*Primary Examiner*—Alan Siegel
*Attorney, Agent, or Firm*—Susan B. Evans

[57] ABSTRACT

This invention relates to a liquid phase process for the preparation of $R_f CHCl_2$ by the selective homogeneous catalytic hydrodechlorination of $R_f CCl_3$ wherein $R_f$ is F, $CF_3$, $(CF_2)_n Cl$ or $(CF_2)_n CF_3$ by reacting the compound with hydrogen while in solution with a Periodic Table Group 8–10 metal complex catalyst which contains tertiary Periodic Table Group 15 ligands, without added base.

9 Claims, No Drawings

HOMOGENEOUS CATALYTIC HYDRODECHLORINATION OF CHLOROCARBONS

BACKGROUND OF THE INVENTION

This invention relates to a liquid phase process for the selective homogeneous catalytic hydrodechlorination of a chlorofluorocarbon compound by reacting the compound with hydrogen while in solution with a Periodic Table Group 8–10 metal complex catalyst which contains tertiary Periodic Table Group 15 ligands without added base.

By Periodic Table Group, Applicant includes those elements organized in Groups described as the "new notation" in the Periodic Table appearing in the CRC Handbook of Chemistry and Physics, 67th Edition, CRC Press (1986–1987).

Chlorofluorocarbons are considered to be detrimental toward the Earth's ozone layer. There is a worldwide effort to develop processes that will replace one or more of the chlorine atom(s) in certain chlorofluorocarbons with hydrogen. For example, 1,1,1,2-tetrafluoroethane (HFC-134a), a hydrofluorocarbon is being considered as a replacement for dichlorodifluoromethane (CFC-12) in refrigeration systems because of its refrigerant properties and zero ozone depletion potential.

There is thus a need for manufacturing processes that provide fluorocarbons that contain less or ideally no chlorine.

One method of reducing the chlorine content of halogen-substituted hydrocarbons containing chlorine as well as fluorine is reacting such organic starting materials with hydrogen in the presence of a hydrogenation catalyst (e.g., supported Periodic Table Groups 7–10 metal catalysts). British Patent Specification 1,578,933 discloses, for example, that HFC-134a can be prepared by the hydrogenolysis of 2,2-dichloro-1,1,1,2-tetrafluoroethane (CFC-114a) or 1,1,1,2-tetrafluorochloroethane (HCFC-124) over palladium on carbon or palladium on alumina hydrogenation catalysts. These processes are typically run in the gas or liquid phase with a solid heterogeneous catalyst.

The prior art (Lokteva et al., Izv. Akad. Nauk. SSSR, Ser. Khim., 1989, (3), 539–42; Ferrughelli and Horvath, J. C. S., Chem. Commun., 1992, 806) teaches hydrodechlorination using soluble homogeneous catalysts which require an excess of added base (NaOH, NEt$_3$) for removal of the HCl product. The present invention requires no added base.

SUMMARY OF THE INVENTION

A process is provided in accordance with this invention for a liquid phase preparation of R$_f$CHCl$_2$ by the selective homogeneous catalytic hydrodechlorination of a compound having the formula R$_f$CCl$_3$ wherein R$_f$ is F, CF$_3$, (CF$_2$)$_n$Cl or (CF$_2$)$_n$CF$_3$, and n is 1–4, which comprises reacting the compound with hydrogen while in a solution with a Periodic Table Group 8, 9 or 10 metal complex containing tertiary Periodic Table Group 15 ligands, preferably phosphines, without added base.

DETAILS OF THE INVENTION

The CFC compounds used in the hydrodechlorination reaction of this invention are preferably those wherein R$_f$ is F, CF$_3$, CF$_2$CF$_3$, CF$_2$Cl, and (CF$_2$)$_4$Cl, more preferably, CF$_3$. Competing 1,2-dechlorination to alkenes is observed when Cl is also on the C bonded to the "CCl$_3$" group.

In accordance with this invention the CFC compounds to be hydrodechlorinated are reacted with hydrogen at a temperature of from about 25° C. to about 100° C., preferably from about 85° C. to about 90° C.

The hydrodechlorination of CFCs is performed in liquid phase using well-known chemical engineering practice, which includes continuous, semi-continuous or batch operations, preferably semi-continuous, to reduce the amount of HCl in solution. The hydrodechlorination process is typically achieved at atmospheric or superatmospheric pressures.

A conventional amount of H$_2$ is used. Generally, in order to provide substantial hydrodechlorination product yields, the amount of hydrogen used is at least stoichiometric.

The reaction is conducted at a H$_2$ pressure of from about 30 to about 1000 psi, preferably about 50 to about 100 psi, more preferably about 100 psi. However, pressure is not a critical factor.

In accordance with this invention the reaction between the chlorocarbon component, H$_2$ and catalyst takes place in solution. Suitable solvents include aromatics such as benzene or toluene and ethers such as THF or DME, preferably benzene or toluene, more preferably benzene.

In accordance with this invention, metal complex catalysts suitable for hydrodechlorination are provided which contain at least one metal, preferably selected from the group consisting of iron, ruthenium, osmium, cobalt, rhodium, iridium, nickel, palladium and platinum. These metal complexes contain tertiary Periodic Table Group 15 ligands selected from phosphines, arsines, stibines and bismuthines. Catalysts are more preferably Fe, Ru, Os, Co, Rh, Ir, Ni, Pd, or Pt with a phosphine ligand, still more preferably a Rh phosphine complex, most preferably RhCl(PPh$_3$)$_3$. The ligand may be of the formula (i) ER$_3$ wherein E is P, As, Sb or Bi, and R is hydrocarbyl or (ii) 1,2-(ER$_2'$)$_2$C$_6$H$_4$ or 1,n-(ER$_2'$)$_2$(CH$_3$)$_n$ where n is 1–6, and R' is hydrocarbyl.

The preferred ligand is of the formula ER$_3$ wherein E is P and R is an aromatic hydrocarbyl.

Hydrocarbyl is a straight chain, branched or cyclic arrangement of carbon atoms connected by single, double or triple bonds, and substituted accordingly with hydrogen atoms. As used herein, hydrocarbyl groups may be aliphatic and/or aromatic.

A base is a non-metal containing compound which forms a salt with the HCl co-product of the hydrodechlorination reaction.

In this specification and the Examples the following abbreviations are used:
CFC—chlorofluorocarbon
HFC—hydrofluorocarbon
THF—tetrahydrofuran
HDC—hydrodechlorination
NMR—nuclear magnetic resonance
GC/MS—gas chromatography/mass spectroscopy
DME—1,2-bis(dimethoxy)ethane
psi—pounds per square inch (1 psi=6.9×10$^3$ Pa)
Ph—C$_6$H$_5$
Pr$^i$—isopropyl, i.e., CH(CH$_3$)$_2$
Hx—n-hexyl, i.e., (CH$_2$)$_5$CH$_3$
Me—methyl
Et—ethyl

EXAMPLES

The following $R_fCCl_3$ hydrodechlorination (HDC) reactions were conducted in a lab reactor consisting of a stirred Fischer-Porter tube, a sparger for introduction of $H_2$, and a back-pressure regulator to allow for continuous removal of HCl as it is formed. The reactor design also allowed for liquid sampling as the reaction proceeds. Unless stated otherwise, all reactions were performed at 85°–90° C. in benzene at a constant pressure of 100 psi $H_2$. Catalyst, solvent and liquid CFC substrate were all loaded into the tube in a nitrogen-purged dry box and the tube sealed with a rubber septum. The tube was attached to the reactor under a flow of argon and the reaction pressurized with $H_2$ and heated. Reaction products were analyzed by $^{19}F$ NMR spectroscopy and, in some cases, GC/MS.

EXAMPLE 1

Example Showing High Selectivity to $CHCl_2CF_3$

A mixture of 465 mg (2.5 mmol) $CCl_3CF_3$ and 46 mg (0.05 mmol) $RhCl(PPh_3)_3$ in 50 mL of dry, distilled benzene was treated with $H_2$ for 4.5 hr to give >95% $CHCl_2CF_3$ at 44.5% conversion (5 turnovers/Rh/hr). No $CH_2ClCF_3$ was detected.

EXAMPLE 2

Catalyst Loading of 0.2 mol %

A mixture of 4.65 g (25 mmol) $CCl_3CF_3$ and 50 mg (0.05 mmol) $RhCl(PPh_3)_3$ in 50 mL of dry, distilled benzene was treated with $H_2$ for 19.5 hr to give >95% $CHCl_2CF_3$ at 33% conversion (total of 167 turnovers/Rh; 8.5 turnovers/Rh/hr). Solution monitoring showed productivities of 17.5 turnovers/Rh/hr during the first hr and 15.5 turnovers/Rh/hr over 4.7 hr.

EXAMPLE 3

Use of Benzene Solvent Avoids H Atom Abstraction

Two reactions were conducted as in Example 1 but wherein the reactant gas was deuterium ($D_2$) instead of hydrogen and the solvent was either benzene or toluene. After 24 hr the toluene reaction went to completion, yielding a 3:1 mixture of $CHCl_2CF_3$ and $CDCl_2CF_3$ whereas in benzene conversion was 55% to give $CDCl_2CF_3$ with only a trace of $CHCl_2CF_3$.

EXAMPLE 4

Using More Electron-Rich Catalyst gives Higher Production

A mixture of 465 mg (2.5 mmol) $CCl_3CF_3$ and 50 mg (0.05 mmol) $RhCl(PPh_2Hx^n)_2$ in 50 mL of dry, distilled benzene was treated with $H_2$ for 4 hr to give >95% $CHCl_2CF_3$ at 96.5% conversion (>8 turnovers/Rh/hr).

EXAMPLE 5

Productivity is Lower with Bulky Trialkylphosphines

A mixture of 465 mg (2.5 mmol) $CCl_3CF_3$ and 25 mg (0.05 mmol) $RhCl(N_2)(PPr^i_3)_2$ in 50 mL of dry, distilled benzene was treated with $H_2$ for 4.5 hr to give >95% $CHCl_2CF_3$ at 11.5% conversion (6 turnovers/Rh).

EXAMPLE 6

Cationic Rh Complex is also Effective

A mixture of 465 mg (2.5 mmol) $CCl_3CF_3$ and 2 mL of a 0.04M tetrahydrofuran (THF) solution of $[Rh(PPh_3)_3]BF_4$ was dissolved in 50 mL of dry, distilled THF and treated with $H_2$ for 24 hr at 25° C. to give >95% $CHCl_2CF_3$ at 73.5% conversion.

EXAMPLE 7

$R_fCCl_3$ is $CCl_3F$

A mixture of 344 mg (2.5 mmol) $CCl_3F$ and 46 mg (0.05 mmol) $RhCl(PPh_3)_3$ in 50 mL of dry, distilled benzene was treated with $H_2$ for 20 hr to give >95% $CHCl_2F$ at 100% conversion (>2.5 turnovers/Rh/hr).

EXAMPLE 8

$R_fCCl_3$ is $CCl_3CF_2CF_3$

A mixture of 328 mg (1.4 mmol) $CCl_3CF_2CF_3$ and 23 mg (0.025 mmol) $RhCl(PPh_3)_3$ in 50 mL of dry, distilled benzene was treated with $H_2$ for 20 hr to give >95% $CHCl_2CF_2CF_3$ at 100% conversion (>2.5 turnovers/Rh/hr).

EXAMPLE 9

$R_fCCl_3$ is $CCl_3(CF_2)_4Cl$

A mixture of 885 mg (2.5 mmol) $CCl_3(CF_2)_4Cl$ and 46 mg (0.05 mmol) $RhCl(PPh_3)_3$ in 50 mL of dry, distilled benzene was treated with $H_2$ for 24 hr to give >95% $CHCl_2(CF_2)_4Cl$ at 100% conversion (>2 turnovers/Rh/hr).

EXAMPLE 10

$R_fCCl_3$ is $CCl_3CF_2Cl$

A mixture of 505 mg (2.5 mmol) $CCl_3CF_2Cl$ and 46 mg (0.05 mmol) $RhCl(PPh_3)_3$ in 50 mL of dry, distilled benzene was treated with $H_2$ for 24 hr to give >90% $CHCl_2CF_2Cl$ at 100% conversion (>2 turnovers/Rh/hr) along with traces of $CCl_2=CF_2$ and $CHCl_2CF_2H$.

EXAMPLE 11

Batch Mode Reactions

The following reactions were conducted in batch mode in a Fischer-Porter tube with liquid sampling to get rough kinetic data and define the influence of $H_2$ pressure. The HCl was not removed.

A mixture of 930 mg (5 mmol) $CCl_3CF_3$ and 50 mg (0.05 mmol) $RhCl(PPh_3)_3$ in 50 mL of dry, distilled benzene was treated with $H_2$ (100, 200 and 500 psi) for 14 hr at 100° C. to give >95% $CHCl_2CF_3$ at 65.5, 70.5 and 69% conversion, respectively. No effect of $H_2$ pressure on the initial rate of hydrodechlorination (ca. 9 turnovers/Rh/hr) was observed.

What is claimed is:

1. A liquid phase process for the preparation of $R_fCHCl_2$ by the selective homogeneous catalytic hydrodechlorination of a compound having the formula $R_fCCl_3$ wherein $R_f$ is F, $CF_3$, $(CF_2)_nCl$ or $(CF_2)_nCF_3$, and n is 1–4 which comprises reacting the compound with hydrogen while in solution with a Periodic Table Group 8–10 metal complex hydrodechlorination catalyst without added base, to form $R_fCHCl_2$, wherein the Group 8–10 metal is selected from the group consisting of Fe, Ru, Os, Co, Rh, Ir, Ni, Pd or Pt, with a tertiary Periodic Table Group 15 ligand selected from the group consisting of phosphine, arsine, stibine, and bismuthine.

2. A process according to claim 1 wherein the temperature is about 25° to about 100° C. and the pressure is about 50 to about 500 psi.

3. A process according to claim 2 wherein the temperature is about 85°–90° C. and the pressure is about psi.

4. A process according to claim 3 wherein $R_f$ is selected from F, $CF_3$, $CF_2Cl$, and $(CF_2)_4Cl$.

5. A process according to claim 4 wherein $R_f$ is $CF_3$.

6. A process according to claim 5 wherein the catalyst is selected from Fe, Ru, Os, Co, Rh, Ir, Ni, Pd, and Pt with phosphine ligands.

7. A process according to claim 6 wherein the catalyst is a Rh phosphine complex.

8. A process according to claim 7 further comprising a solvent selected from benzene, toluene, ether, THF and DME.

9. A liquid phase process for the selective homogeneous catalytic hydrodechlorination of $CF_3CCl_3$ which comprises reacting $CF_3CCl_3$ with $H_2$ while in a benzene solution with a $RhCl(PPh_3)_3$ catalyst at a temperature of 85° C., at a constant pressure of 100 psi to form $CF_3CHCl_2$.

* * * * *